United States Patent
David

(10) Patent No.: US 7,584,645 B2
(45) Date of Patent: Sep. 8, 2009

(54) APPARATUS AND METHOD FOR MEASURING FRICTION FORCES

(75) Inventor: Dominique David, Claix (FR)

(73) Assignee: Commissariat A L'Energie Atomique, Paris (FR)

( * ) Notice: Subject to any disclaimer, the term of this patent is extended or adjusted under 35 U.S.C. 154(b) by 319 days.

(21) Appl. No.: 11/340,624

(22) Filed: Jan. 27, 2006

(65) Prior Publication Data

US 2006/0169023 A1 Aug. 3, 2006

(30) Foreign Application Priority Data

Feb. 3, 2005 (FR) .................................. 05 50311

(51) Int. Cl.
*G01N 19/02* (2006.01)
*G01L 5/16* (2006.01)
*G01L 5/00* (2006.01)
*G01L 1/22* (2006.01)

(52) U.S. Cl. ............................ 73/9; 73/862.044; 702/41
(58) Field of Classification Search .................. 73/9, 73/862.043–862.044, 862.046; 702/41, 190
See application file for complete search history.

(56) References Cited

U.S. PATENT DOCUMENTS

| | | | | | |
|---|---|---|---|---|---|
| 3,324,287 | A | * | 6/1967 | Fetterman et al. | 702/41 |
| 5,375,452 | A | * | 12/1994 | Helldorfer et al. | 73/9 |
| 5,571,973 | A | | 11/1996 | Taylot | 73/862.046 |
| 5,989,199 | A | | 11/1999 | Cundari et al. | 600/587 |
| 6,388,655 | B1 | * | 5/2002 | Leung | 345/157 |
| 6,551,194 | B2 | * | 4/2003 | Hammerquist | 473/145 |
| 2003/0056579 | A1 | | 3/2003 | Poulbot et al. | 73/146 |
| 2003/0160621 | A1 | | 8/2003 | Cresswell et al. | 324/691 |
| 2007/0267229 | A1 | * | 11/2007 | Caritu | 178/19.01 |

FOREIGN PATENT DOCUMENTS

| EP | 444772 A2 * | 9/1991 | 73/9 |
|---|---|---|---|
| EP | 0 970 657 A1 | 1/2000 | |
| FR | 2 811 764 | 1/2002 | |
| GB | 2115556 A * | 9/1983 | 73/862.046 |

OTHER PUBLICATIONS

Pierre-Louis Bossart, "Détection de Contours Réguliers Dans des Images Bruitées Et Texturées", Association des Contours Actifs Et D'une Approche Multiéchelle, Oct. 17, 1994, pp. 60-89, (with English Abstract), cover page and page with English abstract illegible.

Pierre-Louis Bossart, et al., "Detection of Regular Boundaries in Noisy and Texture Images: a Multiscale Active Contour Approach", Traitement du Signal, vol. 14, No. 2, 1997, (with English Abstract), pp. 209-225.

* cited by examiner

*Primary Examiner*—Thomas P Noland
(74) *Attorney, Agent, or Firm*—Oblon, Spivak, McClelland, Maier & Neustadt, P.C.

(57) ABSTRACT

According to an exemplary embodiment, a set of three-dimensional force sensors is used, distributed on one face of a support. Each sensor outputs signals representative of a force applied by an object on this sensor. An electronic processing unit determines components of forces applied on the sensors by the object and also output the relative tangential velocity of at least one point on the object that is in contact with one of the sensors and, advantageously, the point at which the component of the force applied by the object on this sensor and normal to the face of the support, is a maximum.

8 Claims, 2 Drawing Sheets

APPARATUS AND METHOD FOR MEASURING FRICTION FORCES

TECHNICAL FIELD

This invention relates to an apparatus and method for measuring friction forces.

The invention is designed to acquire and characterize friction forces, in other words forces that occur when two objects are moved with respect to each other, while being held in contact with each other.

The invention is used in applications particularly in the following fields:

mats for prevention of skin lesions (particularly seating for the handicapped, anti-bedsore mattresses, soles and shoes), check on adhesion of sliding or rolling objects, for example skis and tires, and characterization of sliding coefficients, for example to define the sliding quality of snow or glass.

STATE OF PRIOR ART

Apparatuses that use an array of uni-dimensional sensors are already known. This array or matrix is capable of supplying an image of the pressure distribution when two objects are brought into contact; for example, it is used to form the image of seating for a handicapped person on his chair.

These known apparatuses have disadvantages. They only measure normal forces, in other words forces applied along an axis perpendicular to the contact surface of the two objects, while relative movement of these objects creates tangential forces parallel to this surface that are additive to the normal forces that occur when the objects are immobile with respect to each other.

Furthermore, the dynamics of these tangential forces is of overriding importance because it determines the nature of the dangerousness of the friction, for example that can cause slipping or lesions.

Remember that friction forces between two objects in contact with each other are applied tangentially and as a first approximation are proportional to the relative velocity of the objects. Therefore, the need for tangential information variable with time can easily be understood.

Refer to the following documents:

[1] EP 0 970 657 A, Apparatus and method for measuring the pressure distribution generated by a three-dimensional object

[2] U.S. Pat. No. 5,571,973 A, Multi-directional piezoresistive shear and normal force sensors for hospital mattresses and seat cushions.

Document [1] describes an array of single dimensional force sensors (in other words force sensors along a single direction), incapable of providing the information mentioned above.

Document [2] describes sensors that are particularly applicable to anti-bedsore mattresses, and which is another application of this invention. However, this document does not disclose an important aspect of this invention, namely a space-time method that is at the heart of estimating friction energies.

No known systems using sensor arrays to measure the pressure applied by one object on another object include any time history processing.

SUMMARY OF THE INVENTION

The purpose of this invention is to overcome the above-mentioned disadvantages.

It aims at measuring the friction forces of one surface on another, and more precisely to create the balance of friction forces present on the contact surface between two objects moving relative to each other.

In particular, the invention is aimed at quantifying areas with a risk, for example a risk of heating, breakage or lesion during such a contact.

To achieve this, the invention proposes to use three-dimensional force sensors (in other words force sensors in three directions perpendicular to each other), these sensors being distributed on the surface of a support, and to use electronic means for processing signals output by these sensors to obtain tangential velocities and consequently friction forces.

Specifically, this invention relates firstly to an apparatus for measuring friction created by an object, this apparatus including:

a set of three-dimensional force sensors distributed on a face of a support, each sensor being designed to output electrical signals representative of a force applied by the object on this sensor, this object possibly moving with respect to the set of sensors or vice versa, and electronic means for processing signals output by the sensors, these electronic processing means being designed to determine components of forces applied on the sensors by the object;

this apparatus being characterized in that the electronic processing means are also designed to output the relative tangential velocity of at least one point on the object that is in contact with one of the sensors.

According to one particular embodiment of the apparatus according to the invention, this point, for which the relative tangential velocity is provided and that is in contact with one of the sensors, is also a point at which the component of the force applied by the object on this sensor and that is normal to the face of the support, is a maximum.

The electronic processing means may also be designed to output the coefficient of friction of the object when it is brought into contact with at least one of the sensors and is moved with respect to this sensor or vice versa.

A texture recognition system can thus be obtained.

Preferably, the sensors are uniformly distributed on the face of the support and thus form an array, or matrix, on this face.

According to a first particular embodiment of the invention, the support on the face on which the sensors are distributed is rigid.

According to a second particular embodiment, the support on the face on which the sensors are distributed is flexible.

The set of sensors may be covered with a layer of elastomer material.

According to one preferred embodiment of the invention, each sensor comprises a deformable membrane fixed to the support and provided with strain gauges, and a rigid rod connected to this membrane, each sensor being designed to output electrical signals representative of a force applied to the rod provided on this sensor.

This invention also relates to a method of measuring the friction of an object, this method using a set of three-dimensional force sensors distributed on one face of a support, each sensor outputting electrical signals representative of a vector force applied by the object on this sensor, this object possibly moving with respect to the set of sensors or vice versa, method in which the signals output by the sensors are processed to determine the components of forces applied on the sensors by the object, this method being characterized in that the relative tangential velocity of at least one point on the object that is in contact with one of the sensors is also determined.

According to one particular embodiment of the method according to the invention, this point for which the relative tangential velocity is determined and that is in contact with one of the sensors, is also a point at which the component of the force applied by the object on this sensor and normal to the face of the support, is a maximum.

Preferably, signals output by the sensors are filtered, a space-time analysis of these signals thus filtered is made to produce a map of instantaneous forces applied to the sensors, and the propagation velocity of the tangential forces applied to these sensors is produced, the points on the contact zone between the object and the sensors at which this velocity is maximum being the points at which maximum energy is produced.

According to one particular embodiment of the method according to the invention, several control objects are beforehand and sequentially moved in contact with the set of sensors or vice versa, to measure the friction of these control objects and memorize their respective textures and roughnesses, and then another object is moved in contact with the set of sensors or vice versa to measure the friction of this other object and to compare its texture and roughness with what was already memorized, in order to recognize this other object.

Preferably, each sensor comprises a deformable membrane fixed to the support and provided with strain gauges, and a rigid rod connected to this membrane, each sensor being designed to output electrical signals representative of a force applied to the rod provided on this sensor.

BRIEF DESCRIPTION OF THE DRAWINGS

This invention will be better understood after reading the description of example embodiments given below, purely for guidance and in no way limitative, with reference to the appended figures, wherein.

DETAILED PRESENTATION OF PARTICULAR EMBODIMENTS

Figure 1:
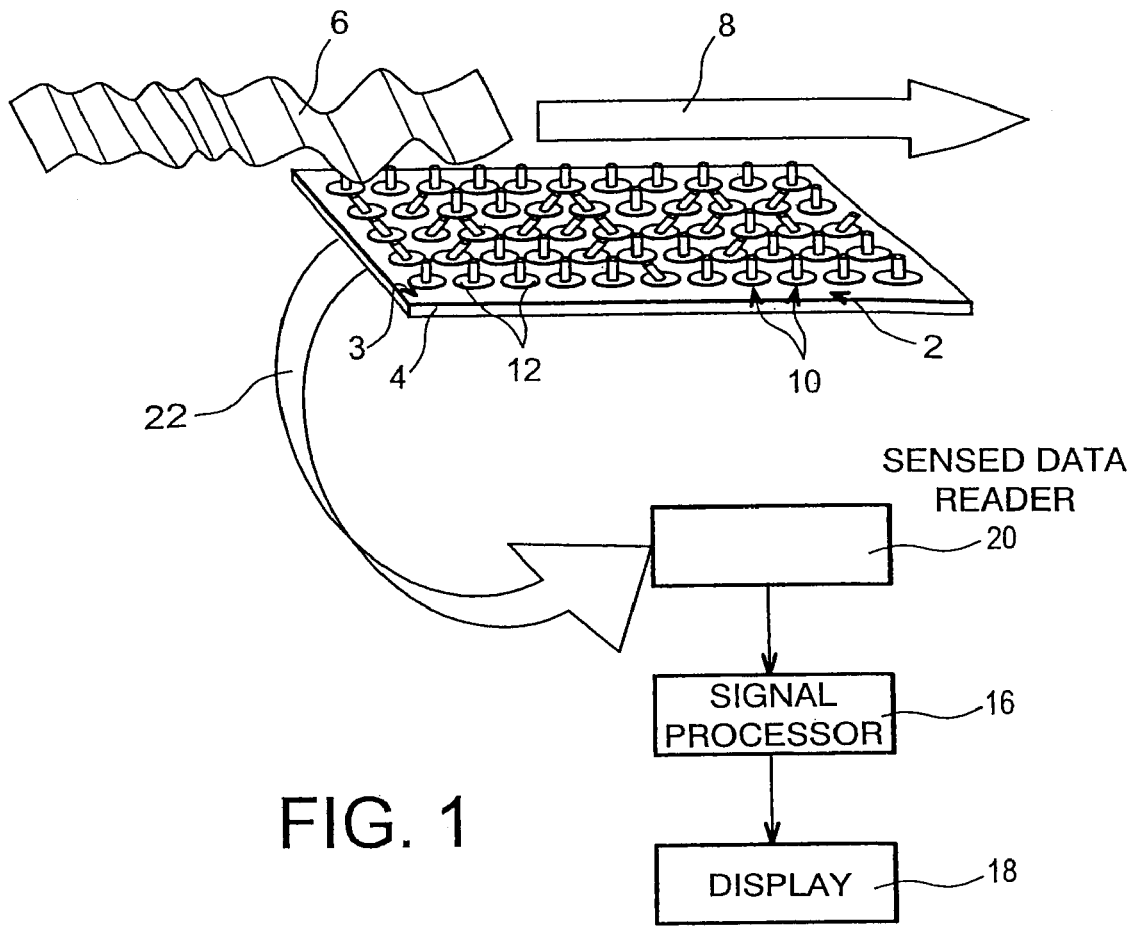
FIG. 1 is a diagrammatic view of a particular embodiment of the apparatus according to the invention.

FIG. 1 is a diagrammatic view of a particular embodiment of the friction measurement apparatus according to the invention.

This apparatus comprises a set 2 of three-dimensional force sensors distributed on a face 3 of a support 4. This support 4 may be rigid, or it may be flexible.

The apparatus makes it possible to measure the friction of an object 6 that is brought into contact with the set 2 of sensors and that is moved with respect to this set, along the arrow 8 in the example shown. However, this is a relative movement; the object 6 may be left immobile, the set 2 may be brought into contact with this object and this set can be moved with respect to the object.

Figure 2:
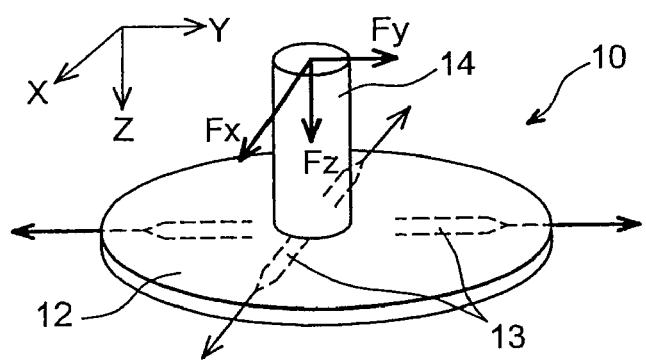
FIG. 2 is a diagrammatic view of a three-dimensional force sensor used in the apparatus in FIG. 1, FIG. 3 diagrammatically shows the steps of a particular embodiment of the method according to the invention.

As can be seen diagrammatically in FIG. 2, each three-dimensional force sensor 10 comprises a deformable membrane 12 provided with strain gauges 13, and a rigid rod 14 connected to this membrane. This membrane is fixed on the face of the support 4 (FIG. 1).

Each sensor outputs electrical signals when the object 6 applies a force onto the rod of this sensor. Processing of these signals makes it possible to determine the three components Fx, Fy, Fz of the force. These three components are measured on three axes perpendicular to each other, two of these axes being parallel to the face 3 of the support 4 while the third axis is perpendicular to this face.

The sensors 10 may be distributed at random on the face 3 of the support 4. However, they are preferably uniformly distributed on this face, as shown in FIG. 1. The sensors then form an array or a matrix on this face.

Such three-dimensional force sensors, also called triaxial force sensors, are disclosed in document:

[3] U.S. Pat. No. 6,666,079 (Poulbot et al.)

The miniature sensors or micro-sensors described in this document each comprise a silicon rod with a diameter of a few tens of micrometers which, when a force is applied to it, creates a local deformation of the membrane on which this rod bears. This deformation is detected by strain gauges installed on this membrane. Recombination (processing) of signals that are then emitted by these strain gauges and are representative of the force, makes it possible to determine the force applied to the silicon rod and more precisely to determine the three components of the force applied on this rod.

However, any other three-dimensional force sensor can be used in the invention provided that it is capable of outputting electrical signals that can be processed to determine the three components of a force applied on this sensor.

The apparatus in FIG. 1 also comprises electronic means 16 of processing signals output by the sensors 10. These electronic means 16 are designed to determine the components of forces applied onto sensor rods by the object 6.

According to the invention, these electronic means 16 are also designed to output the tangential velocity of each point on the object 6 that is in contact with one of the rods 14 and at which a component of the force applied by the object 6 on this rod, is maximum, namely the component which is normal, i.e. orthogonal, to the face 3 of the support 4.

These electronic means 16 are provided with display means 18.

FIG. 1 also shows means 20 of reading data output by the set of sensors 2. These means of reading data, or measurement acquisition means, are connected to electronic processing means 16 to supply the measurements thus, acquired to these electronic processing means.

Furthermore, the connection 22 between the set of sensors and these measurement acquisition means 20 may be a wire connection. However, a wireless connection could also be used.

In this case, the set of sensors is provided with means (not shown) of digitizing electrical signals output by the sensors. The measurements acquired are then transmitted in the form of radiofrequency signals (for example WiFi type signals) to the acquisition means 20 that are then themselves provided with a radiofrequency receiver to detect them.

Preferably, the electronic processing means 16 are also designed to calculate tangential velocities of the other points on the object 6, in other words the points at which the normal component to the face 3 of the support 4 is not maximum.

As will be seen better later, the invention makes it possible to produce a texture recognition system. In this case, the electronic processing means 16 are also designed to provide a map of friction coefficients of the object 6 when the object is brought into contact with the set 2 of sensors 10 and is moved with respect to this set or vice versa.

The apparatus in FIG. 1 provides a means of using a method according to the invention to measure the friction of the object 6.

According to this method, signals output by each sensor 10 are processed to determine the three components of the force applied on the rod 14 of this sensor by the object 6 and the relative tangential velocity is also determined for each point on this object in contact with one of the rods 14 and at which the component of the force applied by the object on this rod, which is normal to face 3 of the support 4, is maximum.

More precisely, this method includes preprocessing of elementary signals respectively emitted by the sensors, and a space-time analysis of the signals thus preprocessed is then made. We will discuss this preprocessing and this space-time analysis again later.

The next step is to produce the instantaneous map of forces, in other words images in which the value of pixels is representative of these vector forces.

The next step is, to produce the propagation dynamics of tangential forces, in other words the propagation velocity of these tangential forces.

Points on the contact area between the object 6 and the rods 14 of the sensors 10 of the set 2, points at which this dynamic is maximum, are then determined. These are points at which energy production is maximum. Therefore these points indicate the potential breakage zones or zones of maximum temperature rise of the object 6, and that need to be monitored.

The following discusses preprocessing of elementary signals output by the sensors 10.

Each sensor 10 outputs up to three signals corresponding to forces measured along three axes X, Y and Z that are advantageously perpendicular to each other. These signals are processed conventionally, respecting signal processing laws. More precisely, these signals are processed taking account of the Shannon's sampling theory for analogue signals.

It should be noted that the apparatus in FIG. 1 involves two sampling methods, namely:

a double space sampling, due to the matrix of sensors 10, and a time sampling, resulting from reading successive values output from this matrix.

These two samplings result in specific preprocessings, namely:

a conventional Shannon filter type filtering, and/or an improvement of the signal/noise ratio, such as matched filtering, and/or Kalman filtering.

Concerning space sampling, these specific preprocessings are related to the spacing of sensors 10 in the matrix and to spatial frequencies resulting from surfaces in contact. For example, one of these surfaces may have roughnesses.

Concerning time sampling, specific preprocessings are related to the sampling frequency and to the frequencies of vibrational phenomena generated by friction between the object 6 and the rods 14 of the sensors 10.

We will now consider the space-time analysis of preprocessed signals. This analysis forms the most important part of the method according to the invention.

The relative movement of surfaces results in an instantaneous map of three-dimensional forces. This map moves at a velocity corresponding to the relative velocity of the object 6 with respect to the set of sensors 10, in other words relative to the support 4.

Furthermore, at the same time this map deforms, particularly as a function of:

the elasticity of surfaces present, namely the surface of the object 6 and the face 3 of the support 4 on which the set of sensors 10 is formed, and transient phenomena due to friction.

For example, the following processing is carried out and is equally valid when the matrix 2 (and more precisely the support 4) is rigid and when it is flexible.

Figure 3:
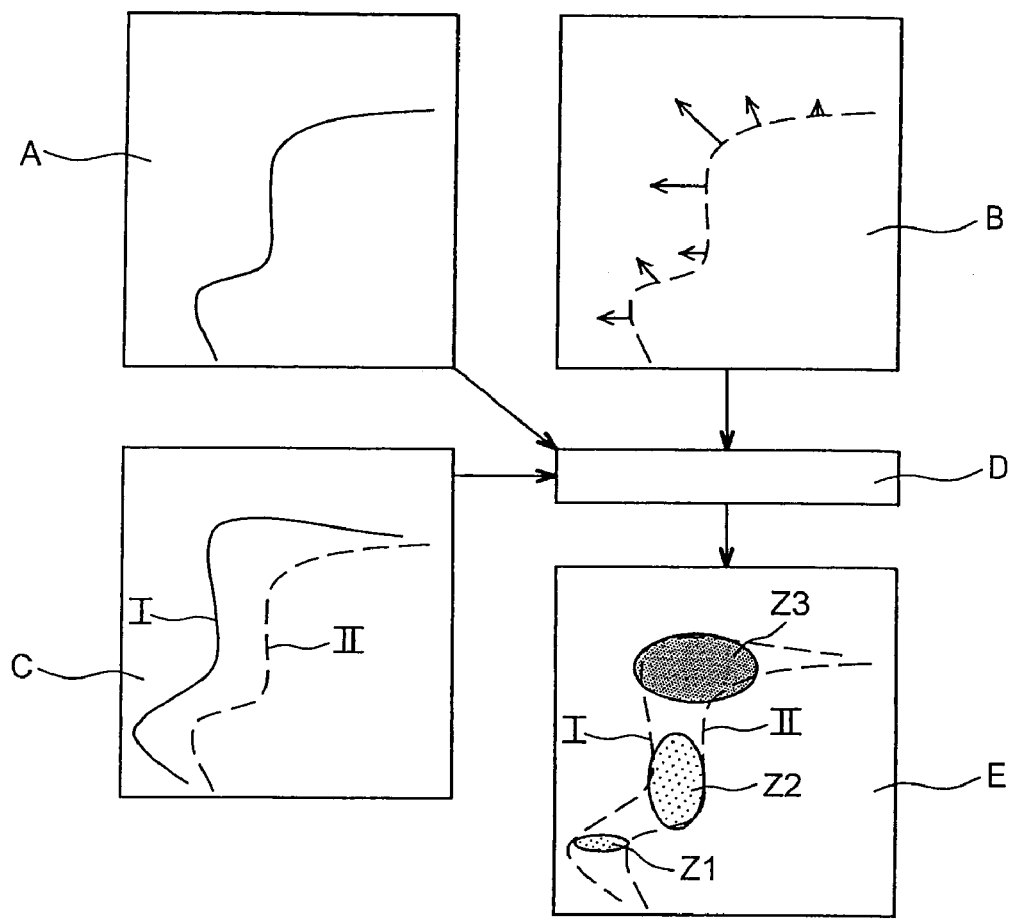

This processing is diagrammatically shown in FIG. 3 that relates to mapping of contact zones.

The map of three-dimensional forces is recorded at the start time t0.

The sub-map of orthogonal forces at time t0 (A in FIG. 3) indicates the contact fronts at which the pressure is maximum. It should be noted that orthogonal forces are measured on the Z axis that is perpendicular to the face 3 of the support 4.

The sub-map of tangential forces at time t0 (B in FIG. 3) shows the propagation direction of maximum contact fronts. The dimension of this sub-map is equal to 2. It should be noted that tangential forces are measured along the axes X and Y that are parallel to the face 3 of the support 4.

The map of vertical forces, or more precisely orthogonal forces, is calculated at time $t1=t0+\Delta t$, where $\Delta t$ represents the time interval between two successive acquisitions of a given sensor and for example is equal to 10 ms (C in FIG. 3 where I represents the map at time t1 and II represents the map at time t0); the support 4 is generally horizontal such that axis Z is generally vertical.

Starting from:

the map of orthogonal forces at time t0, the map of orthogonal forces at time t1, and the map of horizontal forces (or more precisely tangential forces, but the X and Y axes are usually horizontal since the Z axis is generally vertical) at time t0, the map of propagation velocities for maximum contact fronts is calculated.

This is done using a technique for example such as the deformable contour technique that can be used to monitor the variation of a characteristic line (in this case a contact front) of an image when a stress composed of a vector field is applied to this line.

For example, the following document provides information about this subject:

[4] Bossart P. L., Detection of regular contours in noisy and textured images: association of active contours and a multi-scale approach, University Thesis, Signal-Images-Speech, Grenoble (France), Oct. 17 1994.

Another technique consists of using a correlation, possibly by blocks of points, between images at t0 and images at t1.

The propagation velocities thus obtained and combined with values of friction forces denote the zones of energy expenditures in the contact surface and therefore for example potential lesion zones.

In FIG. 3, D represents the space-time analysis that is made from the three maps mentioned above.

Reference E represents the maximum friction energies map at time t1, resulting from this space-time analysis.

In this map, I represents the map at t1, II represents the map at t0, zones Z1, Z2 and Z3 represent zones identified during step D and the energy increases from bottom to top (from zone Z1 to zone Z3).

Advantageously, the above steps may be re-iterated between times t1 and $t2=t1+\Delta t$, and so on between tN and $tN+1=tN+\Delta t$, where N is an integer strictly greater than 2.

A time depth of two consecutive images (tN and $tN+\Delta t$) is usually used. A larger number of successive images can also be combined with predictive methods such as a Kalman filter type of method, which further improves the quality of results.

This invention is also applicable to recognition of a physical texture.

It is useful to be able to automatically recognize such a texture. The objective is then to be able to memorize and then distinguish different materials using an apparatus according to the invention, for example an apparatus of the type shown in FIG. 1.

A recognition method according to the invention consists of creating a relative movement between the object for which the texture is to be recognized and the apparatus, and then recording signals derived from the sensors matrix. The preprocessing step is then carried out.

Several samples (control objects) are submitted to the apparatus during the texture learning phase and are analyzed and then broken down, for example into their principal components. Results are memorized and form a knowledge base (learned textures memory).

The same procedure is followed during the recognition phase, until the breakdown into principal components. Distance calculation methods are then used to select the texture closest to the texture of the studied material, from the system knowledge base.

As a variant, neuron learning techniques can be used that are conventional and form good candidates for recognition processing to be used in the invention.

Whatever the technique which is used, it should be noted that the addition of
- the two tangential components of the contact force, and
- the component of time change of this contact force provides valuable additional information closely related to the roughness of the surface of the object since this roughness creates such tangential forces during the contact (friction).

It should be noted that the learning phase may precede recording and preprocessing steps, carried out with the object for which the texture is to be recognized.

This invention has various advantages. It can also take account of tangential friction forces and the variation of contact forces with time, leading to a much better estimate of friction characteristics than is possible with conventional systems based on a simple map of normal forces.

Furthermore, the apparatus according to the invention is compatible with micro-electronic techniques. Therefore, it can be miniaturized and its manufacturing cost can be reduced.

It should be noted that the density of sensors in the matrix can also be increased and electronic means associated with this matrix can be included (in other words the means may be onboard) in the matrix support, so that an apparatus operating independently can be obtained. It is also possible to transfer electronic acquisition means onto any type of rigid or flexible support.

Figure 4:
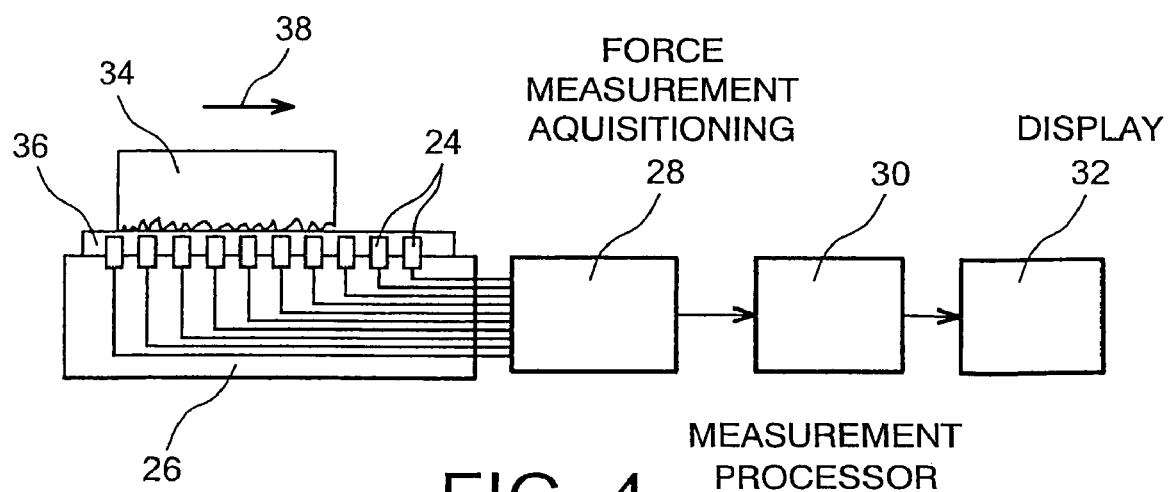
FIG. 4 is a diagrammatic view of another particular embodiment of the apparatus according to the invention.

FIG. 4 is a diagrammatic view of another friction measurement apparatus according to the invention.

This apparatus also includes:
- a set of three-dimensional force sensors 24, this set being formed on a support 26,
- acquisition means 28 of measurements output by this set,
- electronic means 30 for processing the measurements thus acquired and
- means 32 for displaying results output by these electronic means.

FIG. 4 also shows an object 34 for which friction is to be measured according to the invention.

Furthermore, in the example shown in FIG. 4, it is required to determine the characteristics of the texture of this object, and electronic processing means 30 are provided for this purpose.

In this example, the rods of the sensors are not directly brought into contact with the object 34; the set of sensors 24 is covered with an elastomer layer 36, for example PDMS (polydimethylsiloxane), that forms a sort of artificial skin and can be textured to represent fingerprints.

The object 34 is then moved on this layer 36 along the direction of the arrow 38, or the support 26 and therefore this layer 36 is moved on the object that then remains fixed, so as to measure the friction and to characterize the texture of the object 34.

The invention claimed is:

1. An apparatus configured to measure friction created by an object, the apparatus comprising:
    a set of three-dimensional force sensors, distributed on a face of a support, each sensor being configured to output electrical signals representative of a force applied by the object on this sensor, the object moving with respect to the set of sensors or vice versa; and
    electronic means for processing signals output by the sensors, these electronic processing means determining components of forces applied on the sensors by the object,
    wherein the electronic processing means also output relative tangential velocities of points of the object that are in contact with the set of sensors, by making a space-time analysis of the signals emitted by the sensors.

2. The apparatus according to claim 1, wherein the electronic processing means also outputs a coefficient of friction of the object when it is brought into contact with at least one of the sensors and is moved with respect to the at least one of the sensors or vice versa.

3. The apparatus according to claim 1, wherein the sensors are uniformly distributed on the face of the support to form an array, or matrix, on this face.

4. The apparatus according to claim 1, in which the support, on the face on which the sensors are distributed is rigid.

5. The apparatus according to claim 1, in which the support, on the face on which the sensors are distributed is flexible.

6. The apparatus according to claim 1, in which the set of sensors is covered with a layer of elastomer material.

7. The apparatus according to claim 1, wherein each sensor comprises a deformable membrane, fixed to the support and provided with strain gauges, and a rigid rod connected to the deformable membrane, each sensor being configured to output electrical signals representative of a force applied to the rod provided on this sensor.

8. An apparatus configured to measure friction created by an object, the apparatus comprising:
    a set of three-dimensional force sensors, distributed on a face of a support, each sensor being configured to output electrical signals representative of a force applied by the object on this sensor, the object moving with respect to the set of sensors or vice versa; and
    a processing device configured to process signals output by the sensors and to determine components of forces applied on the sensors by the object,
    wherein the processing device is further configured to output relative tangential velocities of points of the object that are in contact with the set of sensors, and at which a component of the force applied by the object on the sensors and that is normal to the face of the support, is a maximum, by making a space-time analysis of the signal emitted by the sensors.

* * * * *